United States Patent
Rothenburger et al.

[19]

[11] Patent Number: 6,121,302
[45] Date of Patent: Sep. 19, 2000

[54] STABILIZATION OF ISOTHIAZOLONE

[75] Inventors: Stephen Jude Rothenburger, Phillipsburg, N.J.; Valerie Lynn Higbee, Delaware Water Gap; Patrick Jay Lutz, Nazareth, both of Pa.

[73] Assignee: Lonza, Inc., Fair Lawn, N.J.

[21] Appl. No.: 09/309,686

[22] Filed: May 11, 1999

[51] Int. Cl.$^7$ ................................................. A61K 31/425
[52] U.S. Cl. ........................ 514/372; 514/373; 514/389
[58] Field of Search ..................... 514/389, 372, 514/373

[56] References Cited

U.S. PATENT DOCUMENTS

| | | | |
|---|---|---|---|
| 3,987,184 | 10/1976 | Foelsch | 514/389 |
| 4,129,448 | 12/1978 | Greenfield et al. | 106/15 R |
| 4,172,140 | 10/1979 | Shull et al. | 424/273 |
| 5,037,989 | 8/1991 | Willingham et al. | 548/213 |
| 5,160,526 | 11/1992 | Ghosh et al. | 71/67 |
| 5,342,836 | 8/1994 | Reeve | 514/242 |
| 5,373,016 | 12/1994 | Brown et al. | 514/372 |
| 5,405,862 | 4/1995 | Farina et al. | 514/389 |
| 5,464,850 | 11/1995 | Voo et al. | 514/372 |

FOREIGN PATENT DOCUMENTS

| | | | |
|---|---|---|---|
| 0 410 609 B1 | 1/1994 | European Pat. Off. | A01N 43/80 |
| 0 411 750 B1 | 5/1994 | European Pat. Off. | A01N 43/80 |
| 4 013 672 | 1/1992 | Japan | C07D 275/03 |

*Primary Examiner*—James H. Reamer
*Attorney, Agent, or Firm*—Darby & Darby

[57] ABSTRACT

The present invention provides a highly stable formulation having broad spectrum preservative properties. The formulation is an admixture of dialkanol-substituted dimethyhydantoin, one or more isothiazolone compounds, a hydantoin stabilizer, and a hydroxyl solvent. The formulation is highly stable in pH ranges of about 4 to 8. Preferably the active components are dimethyloldimethylhydantoin, chloromethylisothiazolone and methylisothiazolone, and the stabilizer dimethylhydantoin. The formulation has a free formaldehyde content of less than 0.2% and is beneficial for preserving various aqueous compositions, including household and industrial products, and especially personal care products, which require a less acidic pH range than in which isothiazolone is stable in the presence of cationic salts.

19 Claims, No Drawings

STABILIZATION OF ISOTHIAZOLONE

FIELD OF THE INVENTION

The present invention relates to stabilized formulations of blended preservative systems comprising isothiazolone, a formaldehyde donor, a stabilizer for isothiazolone, and a hydroxyl solvent, and to methods of use for inhibiting or retarding the growth of microbes in compositions.

BACKGROUND OF THE INVENTION

The need for effective and economical preservative compositions is well known. Many products require preservatives to protect against contamination and growth of microbes, including personal care products such as shampoos, creams, lotions, cosmetics, and soaps, household products such as laundry detergents, hard surface cleaners, fabric softeners, and various industrial products. In particular, personal care product compositions are a nutrient-rich media which benefit from the incorporation of preservatives to control the growth of microorganisms and to prevent spoilage. Generally, the shelf life of these products depends on the resistance to microbial spoilage of components contained therein. It is therefore desirable to formulate a preservative which controls microbial contamination in personal care products, household products, and industrial products.

For the foregoing applications the demand for stable broad-spectrum preservatives has increased. For example, formaldehyde and isothiazolone derivatives have been shown to be highly effective biocidal preservatives. U.S. Pat. No. 3,987,184 issued to Foelsch discloses 1,3-dimethylol-5,5-dimethylhydantoin (DMDMH) as a useful formaldehyde donor compound for the preservation of personal care products, cosmetics, and household and industrial products.

Research in formaldehyde donating compounds has been fruitful. For example, in the case of DMDMH, improved formulations and processing has resulted in compositions which contain very low amounts of free formaldehyde. (See U.S. Pat. No. 5,405,862.) In addition, governmental regulations currently demand low free formaldehyde products. Thus, it would be desirable to formulate a preservative system that contains minimal amounts of free formaldehyde.

Various compositions can be preserved using isothiazolones and DMDMH as a formaldehyde donor. Isothiazolone has never been pre-mixed with a formaldehyde donor in a stabilized mixture, such that the isothiazolone retains its activity as a preservative for any significant period of time, before adding these active components to an end-use product to be preserved. Instead, the actives are added separately to the composition to be preserved. It would be beneficial if a stable isothiazolone preservative system could be designed that contained a mixture of the actives, such that the addition to the end-product could be performed in a single step.

Isothiazolone is highly toxic and very unstable under most circumstances, such as when present in water or other reactive molecule. To make the compound stable large amounts of cationic salts are added and the isothiazolone is diluted (usually to about 14% or less). While under these conditions, isothiazolone is stable at room temperature at low pH (from 1–4). During storage and manufacturing conditions the temperature and pH may increase causing isothiazolone to become unstable. While highly useful for controlling bacteria, fungi and other contaminating microbes in end-use products, isothiazolone's instability under less than ideal conditions results in a marked loss of activity. Thus, it would be advantageous to provide a preservative system that contains isothiazolone which is stable at a broad range of temperature and pH.

Additionally, under very acidic pH conditions, some end-use products such as personal care products cannot be easily formulated with isothiazolone. At less acidic pH levels, comparatively greater amounts of isothiazolone are needed in a preservative formulation because there is some loss of activity. A preservative system should be easy to formulate and have low levels of stable isothiazolone, so that it is nontoxic and non-irritating, but still provides biocidal activity. Stable isothiazolone formulations which are effective at less acidic pH levels have not heretofore been easily obtained.

Furthermore, effective broad spectrum preservative systems that contain formaldehyde donors with low free-formaldehyde and stable isothiazolone for use in applications at less acidic pH levels, free of cationic salts and which are non-toxic are not readily available.

SUMMARY OF THE INVENTION

To overcome the foregoing difficulties in the prior art, it has been discovered that a highly stable, preservative formulation having broad spectrum biocidal activity can be prepared by admixing one or more isothiazolones with a formaldehyde donor, such as alkanol-substituted dimethylhydantoins, and a hydantoin as a stabilizer for isothiazolone.

The stabilized formulations retain their stability at less acidic pH levels and high temperature. The pH of the preservative formulation may be adjusted to pH 4–8 as needed. Thus, a preservative system of the invention will withstand the high temperatures encountered during manufacturing or in warehouse environments. Moreover, high levels of metal salts, which are traditionally used to preserve isothizolone-containing compositions, are not required or even desirable in the compositions of the present invention.

The preservative systems of the invention are especially useful in personal care products, such as shampoos, cosmetics, creams, lotions, and liquid soaps, which have a more neutral pH range (5–7), and remain stable at room and higher temperatures in the absence of high metal salt.

Another advantage is that preservative systems of the invention comply with emerging government regulations, since they have low amounts of free formaldehyde, i.e., less than 0.2%.

It is a further advantage of the invention that a highly stable isothiazolone-containing preservative permits use of less active component, and thus provides a nontoxic, highly effective preservative formulation. Thus, a stabilized preservative system can be more cost-effective, both to the manufacturer and the end user, while providing non-irritating formulations when added to personal care products.

Another advantage of the invention is that the stabilized isothiazolone will remain clear and colorless, even after two months of storage at room temperature in fluorescent light, and remains stable under freeze-thaw conditions.

The invention further provides methods for reducing or inhibiting the growth of microbes in personal care, household, or industrial products by incorporating the stabilized preservative systems of the invention.

DETAILED DESCRIPTION OF THE INVENTION

All patents, patent publications, and literature references cited in this specification are hereby incorporated by reference in their entirety.

A first active component of the stabilized preservative system of the invention comprises one or more 3-isothiazolones having formula I:

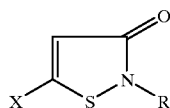

wherein X is hydrogen or halogen, preferably chlorine, and R is an alkyl chain of from 1 to 22 carbon atoms. Preferred isothiazolone components include 5-chloro-2-methyl-4-isothiazolin-3-one (CMI) and 2-methyl-4-isothiazolin-3-one (MI), and mixtures thereof (e.g., CMI/MI). Other 3-isothiazolones can be used in the invention, including 4-chloro-2-methyl-4-isothiazolin-3-one, dichloroisothiazolones such as 4,5-dichloro-2-methyl-4-isothiazolin-3-one, bromoisothiazolones such as 5-bromo-2-methyl-4-isothiazolin-3-one, n-octylisothiazolones such as 2-n-octyl-4-isothiazolin-3-one, and benzisothiazolone.

A second active component of the stabilized preservative system of the invention is a formaldehyde donor, such as hydantoins, N,N"-methylene-bis[N'-(hydroxymethyl)-2,5-dioxo-4-imidazolidinyl]urea, N'-(hydroxymethyl)-N-(1,3-dihydroxymethyl-2,5-dioxo-4-imidazolidinyl]-N'-(hydroxymethyl)urea, and Quaternium-15. Preferred compounds are alkanoldialkyl hydantoins having formula II:

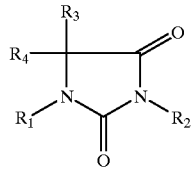

wherein $R_1$ and $R_2$ are each independently hydrogen or $(CH_2)OH$, with the proviso that both $R_1$ and $R_2$ cannot be hydrogen, and $R_3$ and $R_4$ are each independently hydrogen, a methyl group, an ethyl group, a propyl group, or an aryl group.

Alkanol-substituted dimethylhydantoin compounds are preferably used. They include those described in U.S. Pat. No. Nos. 3,987,184 and 4,172,140. These are condensation products of 5,5-dimethylhydantoin with one or more moles of formaldehyde (e.g., 1,3-dimethylol-5,5-dimethylhydantoin, 1-methylol-5,5-dimethylhydantoin, or 3-methylol-5,5-dimethylhydantoin and 1-methylol-3-methyloloxymethylene-5,5-dimethylhydantoin, and mixtures thereof). Mixtures of alkanol-substituted DMH compounds can also be used. Other formaldehyde donors include n-hydroxymethyl-ureas such as imidazolinyl urea and diazolidinyl urea, diaminomethanes, 1,3-oxazolidines, quaternary hexaminium salts such as Quaternium 15, C-methylols, such as Bronopol, 2-bromo-2-nitro-propan-1-ol, and O-hydroxymethyl compounds and formals.

Stabilizers used in the present invention include hydantoins, ureas and derivatives thereof. The hydantoins are represented by formula III:

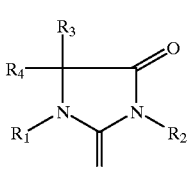

where $R_1$ to $R_4$ are independently selected from H, and a $C_1$ to $C_{22}$ alkyl group.

The N,N"-Methylenebis[N'-2,5-dioxo-4-imidazolidinyl] urea and its derivatives are represented by formula IV:

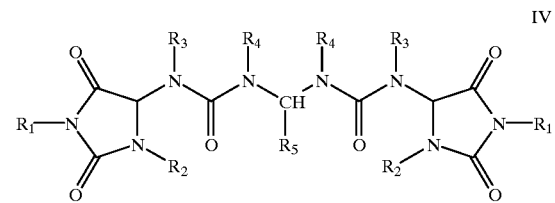

where $R_1$ to $R_5$ are independently selected from H or $C_1$ to $C_{22}$.

The 2,5-Dioxo-4-imidazolidinyl urea (5-ureidohydantoin) and its derivatives are represented by formula V:

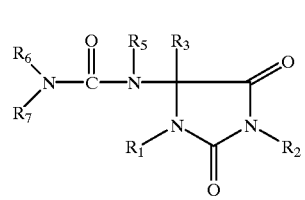

where $R_1$ to $R_7$ are independently selected from H, $CH_3$, $C_2H_5$ or $C_3H_7$.

Urea and its derivatives are represented by formula VI:

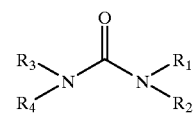

where $R_1$ to $R_4$ are independently selected from H or $C_1$ to $C_{12}$. Where all the R groups are H, the compound is urea.

Preferably, the stabilizer is 5,5-dimethylhydantoin or methylethylhydantoin (MEH).

Water is the preferred solvent for use in the present invention. In addition, a hydroxyl solvent can be used which includes mono-, di-, and polyhydroxyl alcohols. For example, monohydroxyl alcohols having from about 1 to 5 carbon atoms, most preferably ethanol and propanol, may be used. Dihydroxyl alcohols (e.g., glycols) such as $C_2$ to $C_8$ diols (e.g., propylene glycol and butylene glycol) are advantageous. Other compounds which can be used include dipropylene glycol, glycerin, diglycerin, PPG-9, PPG-2-buteth-2, butoxypropanol, butoxydiglycol, PPG-2 butyl ether, glycereth-7, sorbitol, isopentyldiol, myristyl myristate, and phenoxy ethanol.

Table 1 provides ranges for the broad spectrum stabilized formaldehyde donor/isothiazolone preservative concentrates of the invention.

TABLE 1

Broad Spectrum Stabilized Preservative Concentrates

| | Broad wt. % range | Preferred wt. % range |
|---|---|---|
| Dialkanol-substituted DMH | 20 to 95 | 50 to 70 |
| Isothiazolone | 0.02 to 20 | 0.05 to 1.5 |
| Free hydantoin stabilizer (DMH) | 1 to 30 | 5 to 20 |
| Hydroxyl solvent | 0 to 60 | 2 to 45 |
| pH range | 4 to 8 | 5 to 6 |

The ratio of the formaldehyde donor to isothiazolone compound for the broad spectrum concentrate may broadly be from about 5000:1 to 1:1, preferably from about 1000:1 to 5:1. The ratio of the total stabilizer to the isothiazolone compound in the above concentrate may broadly be from about 1:1 to 2000:1, preferably from about 50:1 to 1500:1. This formulation has a free formaldehyde concentration of less than 1 wt. %, preferably less than 0.2 wt. %. Total formaldehyde concentration is from 5 wt. % to 25 wt. %, and preferably from 12 wt. % to 17 wt. %.

A preferred alkanoldialkylhydantoin is 1,3-dimethylol-5,5-dimethylhydantoin (DMDMH), and may be obtained conveniently in a mixture such as Glydant II (Lonza, Inc., Fair Lawn, N.J.), which contains 70% solids (65% DMDMH, 30% monomethyldimethylhydantoin (MMDMH), and 5% dimethylhydantoin (DMH)) and the remainder is water. Glydant II has a total formaldehyde content of 17%.

The preservative concentrates of the invention can be readily prepared in accordance with procedures well known to those skilled in the art, simply by mixing the components set forth in Table 1, supra, and adjusting the pH using any organic or mineral acid (e.g., hydrochloric acid and acetic acid) suitable for the user's purpose. The manner in which the components are mixed can be modified to suit the needs of the formulator, as discussed below, without departing from the spirit of the invention.

The concentration of the active compounds in the use-dilution depends on the nature of the microorganisms to be combated and the composition of the final product to be preserved. For example, the optimum amount of preservative to use for preserving an aqueous composition can be determined by means of screening tests known in the art, and in accordance with the formulation ranges provided in Tables 1 and 2. When preserving an aqueous composition, the use level is generally 0.00005 to 5% by weight, preferably from about 0.01 to 1% of the final composition. Preservative formulations of the invention can also be used directly as they are manufactured without dilution, or in any other manner traditionally used in manufacturing, such as by metering.

In another embodiment of the invention, the stabilizer may be combined with the isothiazolone. A hydroxyl solvent may be added if desired. The resulting composition can be used in making the preservative formulation of the invention by mixing it with a formaldehyde donor.

In the stabilized formulation containing both active ingredients, the stabilizer DMH also serves to minimize the amount of free formaldehyde. However, the amount of DMH typically present in formaldehyde donor compositions is not sufficient to stabilize isothiazolone where the two active ingredients are used. Therefore, when formulating a stabilized preservative of the invention, the total alkyl hydantoin concentration must be considered in determining how much alkyl hydantoin should be added to stabilize the isothiazolone. The total alkyl hydantoin concentration is equal to free alkyl hydantoin plus reacted alkyl hydantoin (e.g., the DMH in the condensation products MMDMH and DMDMH).

The "total" alkyl hydantoin concentration is different from the "added" alkyl hydantoin concentration. Since alkyl hydantoin (free and reacted) may be present in certain formaldehyde donor compositions, an amount of alkyl hydantoin may be added to achieve a stabilizing amount for isothiazolone. Thus, in one embodiment alkyl hydantoin is added to a prepared formaldehyde donor composition (e.g., Glydant II) that contains free and reacted alkyl hydantoin, such that the added alkyl hydantoin in combination with the alkylhydantoin in the formaldehyde donor composition provide a total alkyl hydantoin concentration that stabilizes isothiazolone.

The preservative of the invention is useful for combating microorganisms and, in particular, for the preservation of household, industrial and personal care products, such as cosmetics, lotions, creams, deodorants, shampoos, and soaps. Personal care products include any product that is applied to or contacted with the body of humans or animals in normal use. The following is a list of products that can benefit from incorporation of the preservative system of the invention but is not intended to limit the invention thereto: adhesives, sizes, paper and cardboard, textiles, leather, wood and wood products, paints and articles made of plastic, all purpose liquid cleaners, liquid dishwashing detergent, automotive cleaner, surfactant solutions, household polishes, automotive wax, air freshener, carpet shampoo, pre-spotter, liquid laundry products, pesticide for growing crops, non-food fungicide, non-food herbicide, non-food insecticide, non-food repellent, non-food biopesticide, anti-tarnish products, pre-moistened sponges, pre-moistened mops, coatings, polymer emulsion, natural latex, mineral slurries, pigment slurries, water-based building compounds, caulk, sealer, metal working fluids, metal cleaning fluids, hydraulic fluids, electrodeposition fluids, industrial process water, air washer systems, oil field injection water, liquid hydrocarbon fuels, industrial recirculating cooling water, lubricants, and other materials which can be attacked or decomposed by microorganisms.

Microorganisms which effect contamination or degradation of an aqueous product include bacteria, fungi, yeasts, algae, and slime. Microorganisms of the following genera are examples: Alternaria, such as *Alternaria tenuis*, Aspergillus, such as *Aspergillus niger*, Chaetomium, such as *Chaetomium globosum*, Candida, such as *Candida albicans*, Lentinus, such as *Lentinus tigrinus*, Penicillium, such as *Penicillium glaucum*, Trichophyton, such as *Trichophyton mentagrophytes*, Aureobasidium, such as *Aureobasidium pullulans*, Enterobacter, such as *Enterobacter gergoviae*, Trichoderma, such as *Trichoderma viride*, Escherichia, such as *Escherichia coli*, Pseudomonas, such as *Pseudomonas aeruginosa* and *Burkholderia cepacia*, and Staphylococcus, such as *Staphylococcus aureus* and *Staphylococcus epidermidis*.

The following Example is provided to further teach the invention and is not intended to limit the scope thereof.

EXAMPLE 1

Isothiazolone was tested for stability under accelerated storage conditions and recovery thereof was compared to that of formulations maintained at room temperature (RT). Three test formulations were prepared by mixing 14% isothiazolone (CMI/MI 2.8:1) with Glydant II (Lonza, Inc., Fair Lawn, N.J.), with or without adding a stabilizing amount of DMH, and adjusted to pHs of approximately 5.0, 5.5 and 6.0 using citric acid (CA) or HCl. A total of 9 formulations were prepared having a final concentration of components as described in Table 2. For tests 1–3, the pH was about 5.0. For tests 4–6, the pH was about 5.5 and for tests 7-9, the was about 6.0.

To test the stability of isothiazolone, the nine formulations were subjected to an accelerated stabilizing test at RT and high temperature (54° C.) for a period of 14 days. Thereafter the % recovery of chlormethylisothiazolone (CMI) was determined. See Table 3.

The pH of each test formulation was recorded before and after the 14 day period. The fluctuation in pH for the test formulations was negligible and had an insignificant effect on the recovery of isothiazolone.

TABLE 2

Final concentrations of components used in test formulations

| Component | Tests, 1, 4, 7 (%) | Tests 2, 5, 8 (%) | Tests 3, 6, 9 (%) |
|---|---|---|---|
| Formaldehyde | 15.1 | 15.1 | 15.1 |
| Isothiazolone | 0.048 | 0.048 | 0.048 |
| Added DMH stabilizer | 0 | 8.2 | 8.2 |
| Total DMH stabilizer | 47.0 | 55.2 | 55.2 |
| Isothiazolone:stabilizer | 1:980 | 1:1150 | 1:1150 |
| Acid adjuster | CA | CA | HCl |
| DI Water | qs | qs | qs |
| Target pH | 5, 5.5, 6 | 5, 5.5, 6 | 5, 5.5, 6 |

TABLE 3

Isothiazolone (CMI) Recovery after 14 Day Accelerated Storage

| Test | pH adjuster/ added stabilizer | % recovery CMI after 14 days at RT | % recovery CMI after 14 days at 54° C. | % recovery CMI at 54° C./ % recovery CMI at RT |
|---|---|---|---|---|
| 1 | CA/none | 102 | 94 | 92 |
| 2 | CA/DMH | 97 | 88 | 90 |
| 3 | HCl/DMH | 94 | 96 | 102 |
| 4 | CA/none | 96 | 78 | 81 |
| 5 | CA/DMH | 102 | 88 | 86 |
| 6 | HCl/DMH | 95 | 91 | 96 |
| 7 | CA/none | 108 | 75 | 69 |
| 8 | CA/DMH | 102 | 82 | 80 |
| 9 | HCl/DMH | 95 | 89 | 94 |

Note: Margin of error for rates of recovery is ± 2%. Where rate of recovery is greater than 100%, it was assumed that recovery of isothiazolone was 100%.

Table 3 shows the effectiveness of 5,5-dimethylhydantoin as a stabilizer of isothiazolone in the formulations of the invention. Under accelerated storage conditions, the recovery of stabilized CMI was significantly better than the recovery of CMI which was not stabilized. For example, in test formulation no. 4, the recovery of unstabilized CMI at pH 5.5 (CA as pH adjuster), was 78% under accelerated conditions. However, in test formulation no. 5, when a stabilizing amount of DMH was present, the recovery of CMI increased to 88%. Even greater recoveries were obtained when HCl was the pH adjuster (91% recovery at pH 5.5; see test no. 6, Table 3).

In comparing the recoveries at RT versus accelerated conditions at the various pH levels, it is clear that CMI recovery markedly decreased without stabilization. At about pH 6, which typically causes isothiazolone to break down, the percent recovery of stabilized CMI, using HCl as the pH adjuster, was 95% and 89% at RT and accelerated conditions, respectively. See test no. 9, Table 3. The ratio of recoveries under these conditions was 94%. Recovery of unstabilized CMI with citric acid at about the same pH was 108% (about 100%) and 75% under RT and accelerated storage conditions, respectively. See test no. 7, Table 3. However, the ratio of these recoveries was only 69%. The difference in recoveries under stabilized versus unstabilized conditions is marked, and indicates that DMH greatly improved the stability of isothiazolone at more alkaline pH levels and at higher temperatures. This stabilizing property of DMH could in no way be heretofore predicted.

EXAMPLE 2

This example demonstrates the use of the stabilized preservative formulation of the invention for preserving a typical protein shampoo. The composition of the protein shampoo and the preservative formulation are set forth in Table 4 below. Initially, the pH of the protein shampoo was adjusted to pH 7.0, and the pH preservative formulation was adjusted to a pH of 5.5 using HCl. The preservative formulation was prepared in accordance with the formulation of Table 2 (tests 3, 6 and 9).

TABLE 4

% Composition of Formula Intermediates

| Protein Shampoo | |
|---|---|
| Water Sterile DI | 35.61 |
| Sodium Laureth Sulfate | 35.0 |
| TEA Lauryl Sulfate | 25.0 |
| Cocomide DEA | 3.0 |
| PolyPro 5000 | 1.0 |
| citric acid (50%) | 0.39 |
| Total | 100 |
| Preservative Formulation | |
| Formaldehyde donor composition[1] | 88.5 |
| Isothiazolone (14% CMI/MI)[2] | 0.32 |
| DMH added | 10.0 |
| HCl (10%) | 0.1665 |
| DI Water | 1.0135 |
| Total | 100 |

[1]The formaldehyde donor composition was 35% DMDMH, 30% MMDMH, 5% DMH and 30% water.
[2]The Isothiazolone composition contained a conventional blen of 14% CMI/MI.

Five protein shampoo test formulations were prepared and tested: one without the addition of the preservative formulation and four with varying amounts of the preservative formulation.

The concentrations of protein shampoo and preservative used are represented by formulations 1–5 shown in Table 5:

TABLE 5

% Composition of Protein Shampoo Test Formulations

| Formulation | 1 | 2 | 3 | 4 | 5 |
|---|---|---|---|---|---|
| Protein Shampoo | 100 | 99.8 | 99.9 | 99.95 | 99.975 |
| Preservative | — | 0.2 | 0.1 | 0.05 | 0.025 |
| Total | 100 | 100 | 100 | 100 | 100 |

An equal mixture of S. aureus (ATCC# 6538), E. coli (ATCC #8739), and P. aeruginosa (ATCC# 9027) were added to the shampoo/preservative mixture and the amount of bacteria present was measured (day=0). Measurements were taken at seven day intervals for four weeks and the bacteria levels in each of the five samples were recorded as shown in Table 6.

TABLE 6

Challenge Test Results for Biocide Blend in Protein Shampoo Using Mixed Bacteria

| Formulation | 1 | 2 | 3 | 4 | 5 |
|---|---|---|---|---|---|
| Day 0 | $8.3 \times 10^6$ | $4.5 \times 10^6$ | $8.3 \times 10^6$ | $8.1 \times 10^6$ | $1.1 \times 10^7$ |
| Day 7 | TNTC | <10 | <10 | <10 | <10 |
| Day 14 | TNTC | <10 | <10 | <10 | <10 |
| Day 21 | TNTC | <10 | <10 | <10 | <10 |
| Day 28 | TNTC | <10 | <10 | <10 | <10 |

TNTC = too numerous to count.

As shown by the data in Table 6, the stabilized DMDMH:CMI/MI preservative blend effectively controlled mixed bacteria growth in the protein shampoo at each of the preservative use levels tested.

What is claimed is:

1. A broad spectrum preservative formulation comprising a substituted dimethythydantoin formaldehyde donor, an isothiazolone and an alkyl hydantoin stabilizer, wherein the ratio of the total alkyl hydantoin to isothiazolone is sufficient to stabilize the isothiazolone and the ratio of the formaldehyde donor to isothiazolone is from 5000:1 to 1:1; said formulation havinag a pH of about 4 to 8.

2. The preservative formation of claim 1 wherein the total alkyl hydantoin stabilizer to isothiazolone ratio is from 1:1 to 2000:1.

3. The preservative formulation of claim 1 wherein the formulation contains 20 to 95 wt % of a formaldehyde donor, 0.02 to 90 wt % of an isothiazolone, 1 to 30 wt % of a alkyl hydantoin stabilizer and up to 60 wt % of a hydroxyl solvent.

4. The preservative formulation of claim 1 wherein the formaldehyde donor is a 1,3-dimethylol-5,5-dimethylhydantoin, 1-methylol-5,5-dimethylhydantoin, 3-methylol-5,5-dimethylhydantoin or 1-methylol-3-methyloloxymethylene-5,5-dimethylhydantoin, or mixtures thereof.

5. The preservative formulation of claim 1 wherein the isothiazolone is at least one of the compounds selected from 5-chloro-2-methyl-4-isothiazolin-3-one, 2-methyl-4-isothiazolin-3-one, 4-chloro-2-methyl-4-isothiazolin-3-one, 4,5-dichloro-2-methyl-4-isothiazolin-3-one, 5-bromo-2-methyl-4-isothiazolin-3-one, 2-n-octyl-4-isothiazolin-3-one and benzisothiazolone.

6. The preservative formulation of claim 5 wherein the isothiazolone is a mixture of 5-chloro-2-methyl-4-isothiazolin-3-one and 2-methyl-4-isothiazolin-3-one.

7. The preservative of claim 1 wherein the stabilizer is selected from methylethylhydantoin and dimethylhydantoin.

8. The preservative formulation of claim 1 wherein the components are dissolved in water.

9. The preservative formulation of claim 1 wherein the free formaldehyde concentration is not more than 0.2% and total formaldehyde concentration is at least 5%.

10. A personal care product, household product, or industrial product which contains the compounds in the preservative formulation according to claim 1 in the ratio stated therein.

11. The personal care product of claim 10 selected from shampoos, creams, lotions, soaps, and cosmetics.

12. The personal care product of claim 10 wherein the preservative formulation contains dimethylhydantoin as the stabilizer.

13. An isothiazolone solution comprising isothiazolone and an alkyl hydantoin stabilizer, wherein the ratio of alkyl hydantoin to isothiazolone is 1:1 to 2000:1 and sufficient to stabilize the isothiazolone.

14. The solution of claim 13 wherein the stabilizer is selected from dimethylhydantoin and methylethylhydantoin.

15. The stabilized solution of claim 14 wherein the stabilizer is 5,5-dimethyl hydantoin.

16. The stabilized solution of claim 13 wherein the isothiazolone is 5-chloro-2-methyl-3-isothiazolin-4-one and 2-methyl-3-isothiazolin-4-one.

17. The stabilized solution of claim 13 wherein the pH is from about 4 to 8.

18. A personal care product, household product, or industrial product comprising an antimicrobial-effective amount of a substituted alkyl hydantoin formaldehyde donor, an isothiazolone, and a hydantoin stabilizer for the isothiazolone, wherein the ratio of the formaldehyde donor to isothiazolone is from 5000:1 to 1:1 and the ratio of the stabilizer to isothiazolone is 1:1 to 2000:1 and sufficient to stabilize the isothiazolone; said product having a pH range of from about 5 to 7.

19. A method for preventing the growth of microbes in a composition susceptible to growth comprising adding to said composition a substituted alkyl hydantoin formaldehyde donor, an isothiazolone and an alkyl hydantoin stabilizer wherein the ratio of the alkyl hydantoin to the isothiazolone is sufficient to stabilize the isothiazolone and the ratio of the formaldehyde donor to isothiazolone is from 5000:1 to 1:1 and the pH of said composition is from about 5 to 7.

* * * * *